(12) United States Patent
Lange et al.

(10) Patent No.: US 8,709,353 B2
(45) Date of Patent: Apr. 29, 2014

(54) DEVICE AND METHOD FOR PRODUCING A FLUIDIC CONNECTION BETWEEN CAVITIES

(75) Inventors: Berthold Lange, Werne (DE); Tobias Rodenfels, Dortmund (DE); Wolfgang Stoeters, Muelheim/Ruhr (DE); Markus Voigt, Brackel (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 0 days.

(21) Appl. No.: 13/422,250

(22) Filed: Mar. 16, 2012

(65) Prior Publication Data
US 2013/0071302 A1 Mar. 21, 2013

(30) Foreign Application Priority Data
Mar. 24, 2011 (EP) .................................. 11002439

(51) Int. Cl.
*G01N 33/52* (2006.01)
*B01L 3/00* (2006.01)
*G01N 31/22* (2006.01)
*G01F 3/14* (2006.01)
*G01F 1/08* (2006.01)

(52) U.S. Cl.
USPC ........... 422/430; 422/417; 73/861.82; 73/250

(58) Field of Classification Search
None
See application file for complete search history.

(56) References Cited

U.S. PATENT DOCUMENTS

| 5,652,149 | A | * | 7/1997 | Mileaf et al. ................. 436/518 |
|---|---|---|---|---|
| 5,863,502 | A | * | 1/1999 | Southgate et al. ............ 422/417 |
| 6,293,012 | B1 | * | 9/2001 | Moles ...................... 29/890.124 |
| 6,736,370 | B1 | | 5/2004 | Crockett et al. |
| 6,830,729 | B1 | * | 12/2004 | Holl et al. .................... 422/68.1 |
| 8,171,778 | B2 | * | 5/2012 | Ayliffe .......................... 73/61.71 |
| 8,383,422 | B2 | * | 2/2013 | Katada et al. ................. 436/514 |
| 2002/0166585 | A1 | * | 11/2002 | O'Connor et al. ......... 137/87.01 |
| 2004/0037739 | A1 | * | 2/2004 | McNeely et al. ............... 422/58 |
| 2005/0089449 | A1 | * | 4/2005 | Polwart et al. ................ 422/100 |
| 2013/0071302 | A1 | | 3/2013 | Lange et al. |

FOREIGN PATENT DOCUMENTS

| WO | 0128682 | A1 | 4/2001 |
|---|---|---|---|
| WO | 2004011147 | A1 | 2/2004 |
| WO | 2007064404 | A2 | 6/2007 |
| WO | 2012127049 | A1 | 9/2012 |

OTHER PUBLICATIONS

Chakraborty et al., "MEMS micro-valve for space applications". Sensors and Actuators, vol. 83, 2000, pp. 188-193.
International Search Report and Written Opinion for PCT/EP2012/055263 mailed Jul. 4, 2012.

* cited by examiner

*Primary Examiner* — Jill Warden
*Assistant Examiner* — Brittany Fisher
(74) *Attorney, Agent, or Firm* — Michael P. Morris; Mary-Ellen M. Devlin

(57) ABSTRACT

A device, particularly a microfluidic system, is proposed, in which two cavities are arranged spatially close to one another and are sealed off from one another by a common cover. A fluidic connection can be produced between the cavities by movement of a pin-shaped body towards the cover. In this way it is possible to release a reagent in controlled manner without having to put it under pressure.

12 Claims, 1 Drawing Sheet

DEVICE AND METHOD FOR PRODUCING A FLUIDIC CONNECTION BETWEEN CAVITIES

The present invention relates to a device and a method for producing a fluidic connection.

The present invention relates particularly to microfluidic systems, particularly for diagnosis in microfluidic samples, particularly preferably in so-called point-of-care systems (POC systems). In particular the present invention relates to preferably miniaturised fluidic systems, hereinafter referred to as assays, or immuno-assays, i.e. the investigation of samples using antibodies. However, the invention may also relate to other, particularly miniaturised, fluidic systems. Particularly preferably the present invention relates to so-called cartridge designs, i.e. small, especially box-shaped devices, for the handling and/or examination of an in particular liquid sample or for carrying out assays or immuno-assays.

DE 10 2007 035 721 A1 relates to a microvalve having a first and second valve chamber that can be connected to one another. A membrane that closes off the valve chambers is raised by fluid pressure in one of the chambers, so that a through-channel is formed between the valve chambers. However, there is the disadvantage that a connection between the two valve chambers can only be produced if there is a sufficient pressure difference. Consequently, it is not possible to release a reagent located in one of the chambers with at least substantially no pressure difference, by an external force or by the application of force that is independent of the devices to be connected or controlled independently thereof and/or by microfluidic transport, particularly using capillary forces.

The invention is based on the problem of providing a device and a method for producing a fluidic connection, in which a connection can be produced even without a pressure difference and/or by the external application of force.

The above problem is solved by one or more embodiments disclosed and described herein.

The present invention relates in particular to the release of a reagent or other, particularly liquid or fluidically active substances, particularly in a microfluidic system. By "microfluidic" are meant, according to the invention, volumes of preferably less than 10 ml, particularly preferably less than 1 ml, and/or channel, cavity or liquid cross-sections (maximum and/or hydraulic diameter) of less than 5 mm, preferably less than 2 mm, particularly preferably less than 500 μm.

According to a first aspect of the present invention, a device, particularly a microfluidic system, comprises a substrate and two cavities in spatial relationship with one another. The cavities are sealed off from one another by a common cover. In addition, the device comprises a body preferably in the shape of a pin which is movable from a starting position towards the cover, thereby creating a fluidic connection between the cavities.

In particular, a (microfluidic) valve is formed which can be opened by moving the body into an opening position and can preferably also be closed again, particularly by moving the body back into the starting position. This advantageously allows the fluidic connection to be produced without any pressure difference and the release of a reagent contained in one of the cavities can be controlled.

Particularly preferably, the body is arranged in the substrate, while preferably the body can act on a region of the cover that covers both cavities. The cover can be deformed by the body, preferably by bulging in a convex shape, expanding and/or partially detaching the cover from the substrate, particularly in the region. Preferably, the body is pushed out of the substrate towards the cover, while the cover can be stretched or raised in parts in the manner of a tent. The region of the cover detached from the substrate can form a cavity between the cover and the substrate, particularly a frustum-shaped and/or microfluidically active cavity, which in particular forms the fluidic connection between the cavities.

Preferably, the cavities are arranged or formed in the substrate and can be wholly or partly closed off by the cover. The cavities preferably form microfluidically active channels with the cover, i.e. in particular channels with a cross-section which permits or promotes capillary transport. The cover is preferably arranged on the substrate, more part adhesively bonded and/or welded to the substrate, and may be or may comprise a film, plate or the like.

In the present invention, particularly in the starting position of the body, the cavities are sealed off from one another by the cover, which abuts or adheres in particular in a sealing relationship on an intermediate region of the substrate. For this purpose, the cover may rest on the substrate, at least in a region between the cavities, in a sealing relationship, in interlocking and/or frictional engagement. It is proposed that the cover may be deformed and/or moved between the cavities by the body, forming a fluidic connection, preferably manually, independently of the fluid pressure in the cavities, by the effect of an external, mechanical and/or manual force, and/or by the activation of a device that is independent of the cavities, which may also operate hydraulically or pneumatically.

The body is preferably movable towards the cover to form a fluidic connection between the cavities. A preferably pin-shaped body is used to provide the fluid connection, particularly by raising the cover in a region between the cavities. The substrate may comprise a recess, particularly an opening, in which the body is arranged and/or (slidably) mounted so as to be movable, particularly by being pushed along.

Preferably, the side of the recess remote from the cover is provided with another cover which is able to prevent foreign substances from getting in and/or substances from getting out.

According to another aspect of the present invention, at least one of the cavities may form a storage region, a reservoir or the like or may be connected to one. In order to release a reagent contained in this storage region the cavities are preferably fluidically connected to one another in the manner described at the beginning.

To produce the fluidic connection, preferably a pressure or other force is applied to the preferably pin-shaped body from outside, whereupon the pin-shaped body lifts the cover between the cavities, produces or makes it possible to obtain a hollow space or intermediate space between the substrate and cover (for example together with the pressure of a liquid that is present) and this hollow space acts as a fluidic connection between the cavities. Thus, the reagent contained in the storage region can pass from one cavity into the other, particularly fluidically, without the need for any excess pressure to open a valve in one of the cavities. Advantageously, the release of a reagent or other substance can thus be made possible substantially independently of the cavities, a pressure in the cavities and/or a force acting from outside, particularly a controllable force.

Another aspect of the present invention that can also be achieved independently relates to a method of providing a fluidic connection in a microfluidic arrangement, wherein two adjacent cavities are provided with a common cover such that the cover seals off the cavities from one another, and wherein a fluidic connection between the cavities is established by deforming the cover between the cavities with a preferably pin-shaped body.

Further aspects, features, properties and advantages of the present invention will become apparent from the claims and the following description of a preferred embodiment by reference to the drawings, wherein:

In the Figures, the same reference numerals have been used for identical or similar parts and components, where corresponding or similar advantages and properties are obtained even if there is no repetition of the relevant description.

Figure 1:
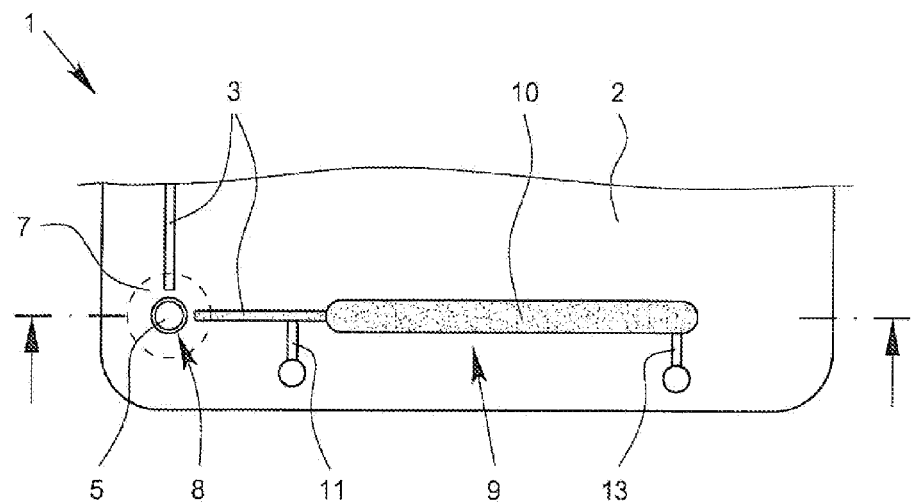
FIG. 1 shows a partial plan view of a device as proposed.

FIG. 1 shows, in a schematic partial plan view, a proposed device 1, particularly a microfluidic system. The device 1 has two cavities 3 which are arranged spatially close or adjacent to one another.

Figure 2:
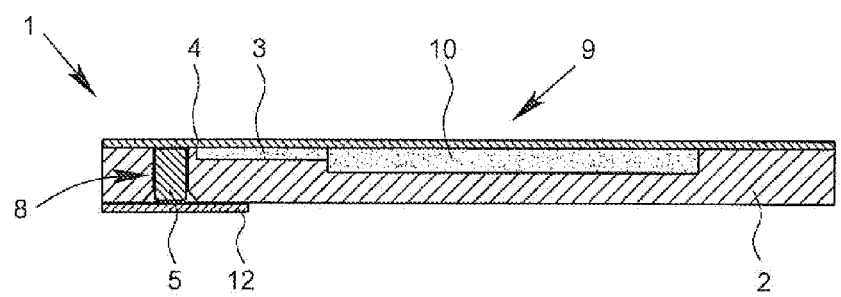
FIG. 2 shows a first section through the device according to FIG. 1.

FIG. 2 shows a section through the device 1 along the section line shown in FIG. 1. The cavities 3 have a common cover 4 which seals off the cavities 3 from one another. This cover 4 is transparent in FIG. 1 or is not shown for technical reasons connected with the representation.

Figure 3:
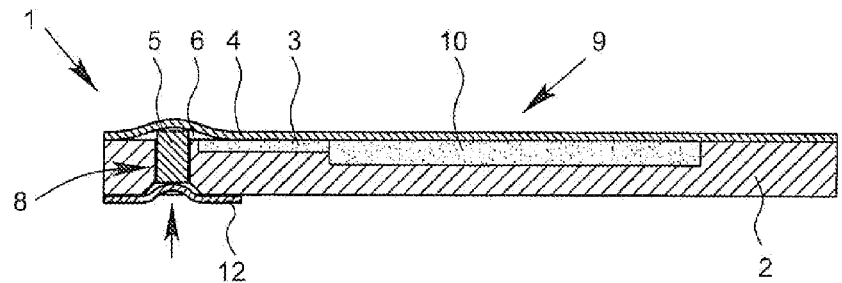
FIG. 3 shows a second section through the device according to FIG. 1.

The device 1 has a preferably pin-shaped body 5. It is proposed that the latter is movable from a starting position as shown by way of example in FIG. 2, in which the cavities 3 are sealed off from one another, towards the cover 4, into an opening position, forming a fluidic connection 6 between the cavities 3. Preferably, the body 5 is pushed or moved for this purpose in the direction indicated by the arrow in FIG. 3 or into the opening position shown in FIG. 3.

Particularly preferably, the body 5 is arranged in a recess 8, particularly an opening, in the substrate 2, preferably movably, more particularly so as to be capable of being pushed along and/or (slidably) mounted or guided. The recess 8 is preferably configured to be at least substantially complementary to the body 5. Advantageously this makes it possible for a reagent 10 to flow through the fluidic connection 6 from one cavity into the other 3, without the recess 8 being substantially filled with reagent 10 or with a considerable quantity of reagent. The recess 8 preferably extends transversely, particularly perpendicularly, to the main directional plane of the cover 4 and/or the substrate 2. This allows the body 5 to move transversely or at least substantially perpendicularly towards the cover 4, thus promoting the preferred detachment of the cover 4 from the substrate 2 to form the connection 6 in the region of the cavities 3.

The body 5 is preferably of cylindrical configuration. This allows the body 5 to be inserted in the recess 8 independently of the rotational position of the body 5 in relation to its central axis perpendicularly to the main directional plane of the substrate 2 and/or cover 4.

The body 5 may be movable towards the cover 4 by translation and/or by a force acting on the body 5 in the direction of the cover 4. Preferably, an external and/or mechanical pressure or other external force on the side of the body 5 remote from the cover 4 causes the body 5 to be pushed from its starting position into its opening position to form the connection 6, as indicated by the arrow in FIG. 3.

The body 5 may be configured with a blunt or flat end facing the cover 4. As a result, the pressure exerted by the body 5 on the cover 4 in order to form the connection 6 can be distributed over an area that corresponds at least substantially to the end surface of the body 5. Thus the occurrence of shear stresses and adverse effects on the cover 4 caused by the body 5 can be avoided.

In the embodiment shown the body 5 may have a diameter of less than 5 mm, less than 2 mm, preferably 1 mm or less.

The length of the body 5 perpendicular to the main directional plane of the cover 4 and/or substrate 2 is preferably less than 10 mm or 5 mm, particularly less than 2 mm. The region 7 may for example have a diameter of less than 10 mm, preferably less than 5 mm, particularly 2 mm or less.

It is particularly preferable if the cover 4 can be reversibly extended by the body 5. It is possible for the extended cover 4 to exert a restoring force on the body 5; in particular the restoring force is capable of moving the body 5 into its starting position (cf. FIG. 2) and/or maintaining it in a starting position. A body 5 that has been moved out towards the cover 4 is thus preferably held in the position shown in FIG. 2 by the tension and/or elasticity of the cover 4 and/or is pressed back from the position shown in FIG. 3 into the position of FIG. 2.

In the starting position of the body 5 (FIG. 2) the cavities 3 are preferably sealed off from one another. If the body 5 is moved out towards the cover 4 (FIG. 3) the fluidic connection 6 is formed. When the force moving the body 5 out is removed the body 5 is preferably pushed back into its starting position (FIG. 2), which leads in particular to a re-establishment of the connection 6 and/or a sealing of the cavities 3 from one another. Alternatively, a permanent connection 6 may be produced by moving the body 5 into the opening position.

A region 7 of the cover 4 particularly preferably covers the recess 8 and/or ends of the two cavities 3. The region 7 may be arranged in particular around the recess 8 and/or the body 5, as indicated by the broken line in FIG. 1.

The cover 4 is preferably deformable in the region 7 by the body 5, in particular by expansion and/or with partial detachment of the cover 4 from the substrate 2, in order to connect the cavities 3 fluidically to one another.

The region 7 of the cover 4 is preferably formed from the same material as the rest of the cover 4. In particular, the region 7 of the cover 4 is formed in one piece with the cover 4 outside the region 7. Alternatively or additionally, the cover 4 may have a different material and/or different geometric properties in the region 7. In particular, the cover 4 may be thicker or thinner in the region 7 than the cover 4 in an area surrounding the region 7.

The cover 4 may have corrugations, expansion pleats or the like in at least parts of the region 7. In particular, a bead, a seal or the like may be formed on or by the cover 4, particularly on the side of the cover 4 facing the substrate 2, in the region 7 of the cover 4, preferably between the recess 8 and the cavities 3.

The cover 4 may be coated with an adhesive and/or sealant in the region 7. Preferably, the cover 4 may have a coating in the region 7, which differs, in particular, from a coating in other parts of the cover 4. The region 7 may have a coating that prevents welding, adhesion or other permanent bonding of the cover 4 to the substrate 2 in the region 7, particularly during manufacture, and/or promotes a later detachment of the cover 4 from the substrate 2 in the region 7. Thus it is preferable for the cover 4 to be configured, at least in the region 7, so as to enable a seal to be formed between the cavities 3 and/or to enable non-destructive detachment of the cover 4 from the substrate 2.

According to another aspect of the present invention, the device 1 preferably comprises, on the side of the substrate 2 remote from the cover 4, an additional cover 12 that covers and/or seals off the recess 8. The additional cover 12 may be adhesively bonded or welded to the substrate 2, in particular. It is preferably configured so as to transmit or transfer a force onto the body 5, particularly pressure and/or by deformation. As indicated by the arrow in FIG. 3, a force may act on the body 5 via the additional cover 12, while preferably the body 5 is pushed against the cover 4. In this way, the cover 4 is able to detach itself from the substrate 2 and/or form a convexity in the region 7, leading to the formation of the fluidic connection 6. The additional cover 12 can prevent foreign matter from entering the recess 8 and/or prevent reagent 10 from escaping, particularly from one of the cavities 3, through the recess 8 on the side of the substrate 2 remote from the cover 4.

On the side of the substrate 2 remote from the cover 4 the recess 8 may have a conical entry portion, particularly with a diameter that increases towards the opening. This makes it possible to exert mechanical, particularly manual pressure, as indicated by the arrow in FIG. 3, and/or reduces the shear stress on the opening edges at the entrance to the recess 8, on the side of the substrate remote from the cover 4. In addition, the insertion of the body 5 into the recess 8 is made easier.

The cover 4 and/or the additional cover 12 may be or may comprise a cover film, the cover 4 and/or 12 preferably being single-ply, multi-ply, adhesive on one side or on both sides, single-layered or multi-layered, with at least one low-melting layer or coating, deformable, elastic and/or flexible.

In particular, the cover 4 and/or 12 may be multi-layered, while in the region 7 one of the layers is omitted and/or an additional layer is provided, the additional layer in particular having elastically resilient properties. Moreover, the cover 4 and/or 12 may have a low-melting layer or coating, particularly a layer that melts below 200° C., particularly below 150° C. This low-melting layer is preferably arranged on the side of the cover 4 and/or 12 facing the substrate 2 and may be used for welding and/or thermally adhering the cover 4 and/or 12 to the substrate 2. Alternatively or additionally, a layer may be provided that is adhesive on one or both sides, particularly on the side of the cover 4 and/or 12 facing the substrate 2, which contributes to a simple and inexpensive mounting of the cover 4 and/or the additional cover 12.

According to one aspect of the present invention the device 1 may have a storage region 9, particularly a reservoir, which is formed with a cavity 3 covered by the cover 4, and/or is connected to the cavity 3 so as to communicate therewith. The storage region 9 may contain a liquid and/or solid reagent 10. It is particularly preferred if the reagent 10 is fluidically transportable, i.e. can be conveyed by capillary forces or the like.

A reagent 10 according to the present invention may be any substance that is capable of interacting preferably with another substance, particularly a sample and/or liquid. The term "reagent" is thus preferably to be understood broadly and also encompasses solvents, detergents or the like. A "reaction" can thus be, in particular, a purely physical or physical-chemical effect of two substances on one another, particularly a dissolution process of a solid or liquid reagent.

The storage region 9 may have an access point 11 and/or a vent 13. The access point 11 and/or the vent 13 may be used to add a liquid or solid reagent 10 and/or to ventilate or exhaust the storage region 9. The access point 11 and/or the vent 13 are preferably adapted to be closed off, particularly by adhesive bonding, adhesion of a film, an adhesive strip and/or by welding. When the storage region 9 is being filled with or drained of a reagent 10, it is possible to use the access point 11 for venting and/or the vent 13 as an access point.

As explained at the beginning, the body 5 is preferably moved from outside and/or mechanically out of the recess 8 in the substrate 2 that comprises the cavities 3, towards the cover 4, such that the cover 4 is lifted away or sheared off from the substrate 2 between the cavities 3 and a fluidic connection 6 is provided between the cavities 3. However, alternatively or additionally, it is also possible for the body 5 to be set in motion by some other method.

In one embodiment, the body 5 may comprise a magnetic material and be moved out of the substrate 2 in the direction of the cover 4 by magnetic repulsion and/or attraction. An electrically conductive arrangement, particularly a coil, which can preferably be used to move the body 5 magnetically and/or electrostatically may be arranged on, in or close to the substrate 2, preferably in the region 7 and/or around the recess 8 or the body 5. Alternatively or additionally, the body 5 may be moved hydraulically or pneumatically. For example, a gas and/or liquid access may be provided to the recess 8 in the substrate 2 and/or to the side of the additional cover 12 remote from the body 5 in order to exert a hydraulic or pneumatic pressure on the body 5, particularly in the direction indicated by the arrow in FIG. 3. However, other alternative possibilities for driving the body 5 are also conceivable.

According to another aspect of the present invention that can also be implemented independently, the proposed device may also be used as an, in particular, microfluidic pump, or to form such a pump. For this, it is preferable for the proposed device to be combined with a non-return valve or other device that inhibits the flow of material in one direction, particularly as disclosed in DE 10 2007 035 721 A1.

By pushing the body 5 into its opening position (FIG. 3) and thereby forming a hollow space, the fluidic connection 6 is created. The additional volume may produce a reduced pressure which causes the reagent 10 to be aspirated as the fluidic connection 6 is created. As the body 5 is moved into its starting position (FIG. 2) the volume of the hollow space produced by the fluidic connection 6 is reduced and any reagent 10 contained in the fluidic connection 6 is forced out of the region 7. If the reagent 10 is prevented from flowing back in one direction, for example by a valve, the reagent 10 is conveyed out of the fluidic connection 6 in the opposite direction.

By repeatedly actuating or moving the body 5 between the starting position and the opening position, the proposed device 1 may thus be used for pumping.

LIST OF REFERENCE NUMERALS 1 device
2 substrate
3 cavity
4 cover
5 body
6 connection
7 region
8 recess
9 storage region
10 reagent
11 access point
12 additional cover
13 vent

The invention claimed is:

1. A device, comprising:

A substrate having first and second spaced apart surfaces;

First and second adjacent cavities extending from the first surface into a thickness of the substrate and laterally along the substrate;

A recess extending through the substrate transversely with respect to, and opening at, the first surface proximate to the first and second adjacent cavities;

body that is movable within the recess and having a distal end that is movable: (i) from a first position at which the distal end is within the recess and not extending out of the opening of the recess, (ii) toward the first surface of the substrate, and (iii) to a second position at which the distal end is extending out of the opening of the recess;

A flexible cover overlying at least a portion of the first surface of the substrate, the first and second cavities, the recess, and the distal end of the body, Wherein: (i) the cover prevents a fluid connection between the first and second cavities when the body is in the first position, and (ii) the distal end of the body distorts the cover by expansion and/or with partial bulging or detachment and causes the cover to move away from the first surface of the substrate in the vicinity of the first and second cavities when the body is in the second position, thereby creating a fluid connection between the first and second cavities between the substrate and the cover.

2. The device according to claim 1, wherein the first and second cavities are arranged or formed in the substrate transversely to one another.

3. The device according to claim 1, wherein the cover rests on or adheres to the substrate at least in a region between the cavities.

4. The device according to claim 1, wherein the cover is of film-like configuration or is a covering film.

5. The device according to claim 1, wherein the distal end of the body is provided with a blunt, flat, or rounded end facing the cover.

6. The device according to claim 1, wherein:
The cavity extends through the substrate between the first and second surfaces thereof, and
The body is movable towards the cover by a translational movement and/or by a force acting on the body in the direction of the cover, by external pressure on a proximate end of the body remote from the cover.

7. The device according to claim 1, wherein the cover is reversibly expandable by the body, while the expanded cover exerts a restoring force on the distal end of the body, and in particular the body is moved into the first position by the restoring force.

8. The device according to claim 1, wherein the recess extends through the substrate and opens at the first and second surfaces thereof.

9. The device according to claim 8, wherein the recess and/or direction of movement of the body extends at least one of transversely and perpendicularly, with respect to a main directional place of the cover and/or the first surface of the substrate.

10. The device according to claim 8, further comprising an additional cover that covers and/or seals off the opening of the recess at the second surface of the substrate, wherein the additional cover is embodied to be elastically or irreversibly deformable in order to transmit a force or pressure to the body.

11. The device according to claim 1, wherein a storage region is formed with a further cavity covered by the cover and/or the storage region is connected to one of the first and second cavities so as to fluidly communicate therewith, the storage region containing a liquid and/or solid reagent.

12. The device according to claim 11, wherein the storage region has a closable access point and/or a closable vent in the cover, wherein the liquid or solid reagent may be added through the access point and/or the vent, and/or the access point and/or the vent is closable by adhesive bonding by adhesion of a film or an adhesive strip and/or by welding.

* * * * *